United States Patent [19]
Brennan

[11] Patent Number: 5,094,233
[45] Date of Patent: Mar. 10, 1992

[54] TURBINATE SHEATH DEVICE

[76] Inventor: Louis G. Brennan, 2800 N. California, Ste. 16, Stockton, Calif. 95204

[21] Appl. No.: 640,150

[22] Filed: Jan. 11, 1991

[51] Int. Cl.$^5$ .................................. A61F 5/04
[52] U.S. Cl. ................................ 602/6; 606/199; 602/17
[58] Field of Search ............ 606/199, 196; 128/89 R, 128/89 A, 87 R, 858, 76 C; 604/94, 285

[56] References Cited
U.S. PATENT DOCUMENTS

| | | | |
|---|---|---|---|
| 3,935,859 | 2/1976 | Doyle | 128/89 R |
| 4,592,356 | 6/1986 | Ersek | 128/342 |
| 4,646,739 | 3/1987 | Doyle | 128/325 |

FOREIGN PATENT DOCUMENTS

| | | | |
|---|---|---|---|
| 1344315 | 10/1987 | U.S.S.R. | 606/199 |
| 1360694 | 12/1987 | U.S.S.R. | 606/199 |

OTHER PUBLICATIONS

"Xomed Rhinology Products" Brochure AD-0057 Nov. 1986 Xomed, Inc.

*Primary Examiner*—C. Fred Rosenbaum
*Assistant Examiner*—Ronald Stright, Jr.

[57] ABSTRACT

Recovery from human ethmoidectomy or other pan-sinus surgery wherein the human middle turbinate is subjected to surgical procedure is improved by a post-operative healing technique which comprises inserting over at least a portion of the post-operative middle turbinate a turbinate sheath device. The novel turbinate sheath comprises a septal plate member having an integrally formed turbinate sheathing portion extending along an outer surface of said rear plate portion in a substantially horizontal position, said turbinate sheathing portion having an upper open slot portion adapted to receive and hold the middle turbinate during post-operative healing. The turbinate sheath device is secured by attaching the septal plate member to a nasal portion during healing, whereby the middle turbinate is separated from the septum and lateral nasal wall to prevent adhesion.

11 Claims, 2 Drawing Sheets

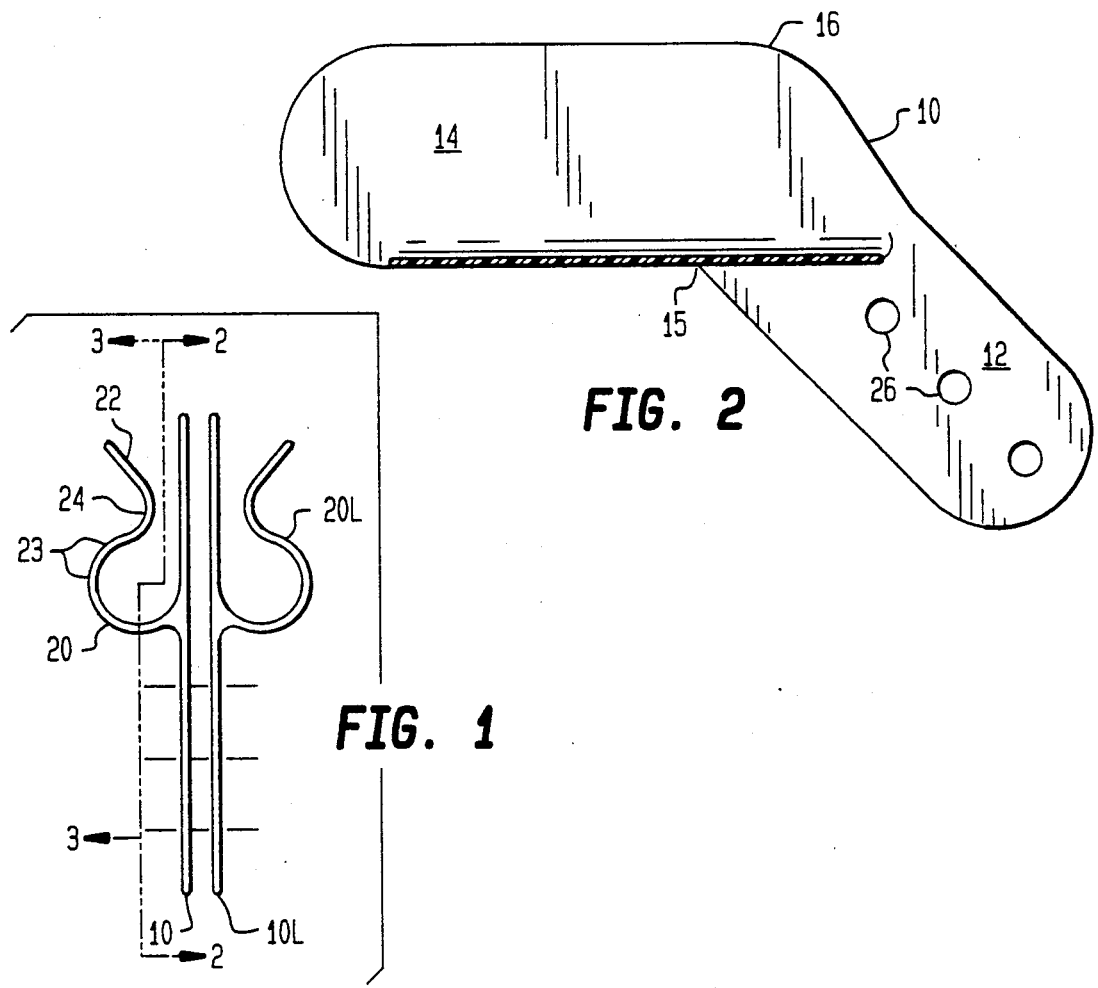
FIG. 2
FIG. 1
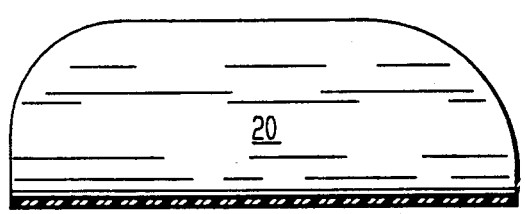
FIG. 3
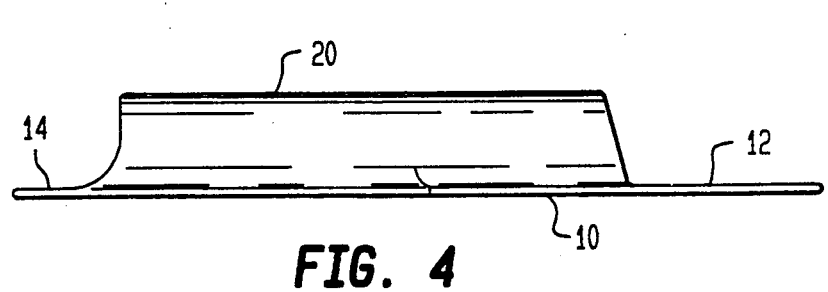
FIG. 4

TURBINATE SHEATH DEVICE

TECHNICAL FIELD

This invention relates to endoscopic sinus surgery techniques. In particular, it relates to a sheath device for post-operative use to prevent adhesion of the middle turbinate during healing.

BACKGROUND OF THE INVENTION

Recent developments in the field of endoscopic surgical techniques and medical devices have provided the skilled otorhinolaryngologist with instrumentation and methods to perform complex paranasal sinus surgical procedures. Improved visualization of the nasal cavity and paranasal sinuses now make these anatomical areas more accessible to the endoscopic surgeon. Surgical guidelines for performing these operations are described in "Endoscopic Paranasal Sinus Surgery" by D. Rice and S. Schaefer, Raven Press, 1988) and in the writings of M. E. Wigand, Messerklinger and Stamberger. Various procedures, such as anterior and posterior ethmoidectomy, sphenoidectomy, maxillary antrostomy, frontal sinusotomy, etc., may be performed in these areas.

For instance, the Wigand procedure typically involves transection of the middle turbinate, beginning with the posterior aspect, visualization of the sphenoid ostium and opening of the posterior ethmoid cells for subsequent surgery. In the sphenoidectomy step, the ostium of the sphenoid is identified and the anterior wall of the sinus removed. Following this step, the posterior ethmoid cells may be entered at their junction with the sphenoid and the fovea ethmoidalis can be identified as an anatomical landmark for further dissection. In anterior ethmoidectomy, the exenteration of the ethmoids is carried anteriorly to the frontal recess. Complications, such as hemorrage, infection, perforation of the fovea ethmoidalis or lamina papyracea, and scarring or adhesion of the middle turbinate, are reported in connection with these procedures.

A particular problem encountered by the endoscopic surgeon has been postoperative adhesion occurring between the middle turbinate and adjacent nasal areas, such as medial adhesion to the septum and lateral adhesion to the lateral nasal wall in the area of the ethmoid sinuses. Otherwise successful surgical procedures may have poor results in these cases. Some surgeons have proposed amputation of the lower half of the middle turbinate at the conclusion of surgery to avoid this complication, resulting in protracted morbidity (crust formation and nasal hygiene problems). The turbinate adhesion problem detracts from an otherwise refined endoscopic surgical procedure.

In an attempt to avoid adhesions, surgeons may often pack the operative site with non-fiber, hydratable and expandable packing, or other materials such as tampons. A "sinus pack" tampon, such as disclosed in U.S. Pat. No. 4,646,739, may be used for short term packing of the operative site; however, risk of 'toxic shock syndrome' after only a day or two is significant. The use of post-operative packing, such as "Merocel Sinus-Pak", is reported to prevent lateralization of the middle turbinate while packing the osteomeatal complex. Packing can displace the middle turbinate in a medial direction and carries with it a significant risk of having the turbinate adhere to the nasal septum, with resultant airway obstruction. While various septal splints can prevent adhesions to the nasal septum, adhesions of the lateral aspect of the middle turbinate to the lateral ethmoid sinus wall are not prevented concurrently.

It is an object of the present invention to provide a sheath device for application to the post-operative middle turbinate, which is effective to prevent both nasal septum and side wall adhesion for at least seven days during healing.

SUMMARY OF THE INVENTION

A novel endoscopic nasal surgery method and medical device have been discovered, wherein the human middle turbinate, contiguous paranasal sinuses and/or nasal septum is subjected to surgical procedure(s) and then protected by a flexible, glove-like turbinate sheath device. The improved post-operative healing technique comprises applying to the post-operative middle turbinate through opposite nasal passages a pair of resilient septal plate members adapted for insertion on opposite sides of the nasal septum, each of the septal plate members having an integrally formed turbinate sheathing portion extending along an outer surface of the plate member in a substantially horizontal position. The turbinate sheathing portion is generally molded plastic and U-shaped with an upper open slot portion adapted to receive and hold the middle turbinate during post-operative healing, with the turbinate sheathing portion extending outwardly from the plate member at a mid-portion thereof with a reverse curved sheathing wall laterally spaced from the rear plate portion to form said slot portion. The sheathing wall has an elongated horizontal portion adapted to grip the middle turbinate and an outward flare portion is adapted to guide the turbinate sheathing portion over the middle turbinate during insertion. The improved procedure is completed by securing the pair of septal plate members in position overlying the middle turbinate, thereby separating the middle turbinate from the nasal septum to prevent medial adhesion and separating the middle turbinate from the nasal wall to prevent lateral adhesion during healing.

The device may be formed of medically acceptable, thermoplastic, flexible fluoroethylene polymer or the like. This technique is particularly useful in pan-sinus surgery involving macroscopy, microscopy or endoscopy, such as ethmoidectomy, maxillary antrostomy and frontal sinusotomy, wherein the middle turbinate can be temporarily encased in a medical grade, non-toxic thermoplastic sheathing device following surgery.

These and other features and advantages of the invention will be understood from the following description and the drawing.

THE DRAWING

FIG. 1 is an end view of a pair of turbinate sheath elements;

FIG. 2 is a cross-sectional side view of a turbinate sheath taken along line 2—2 of FIG. 1;

FIG. 3 is a vertical cross-section view taken along line 3—3 of FIG. 1;

FIG. 4 is a bottom view of a turbinate sheath element;

DESCRIPTION OF PREFERRED EMBODIMENTS AND BEST MODE

Figure 5:
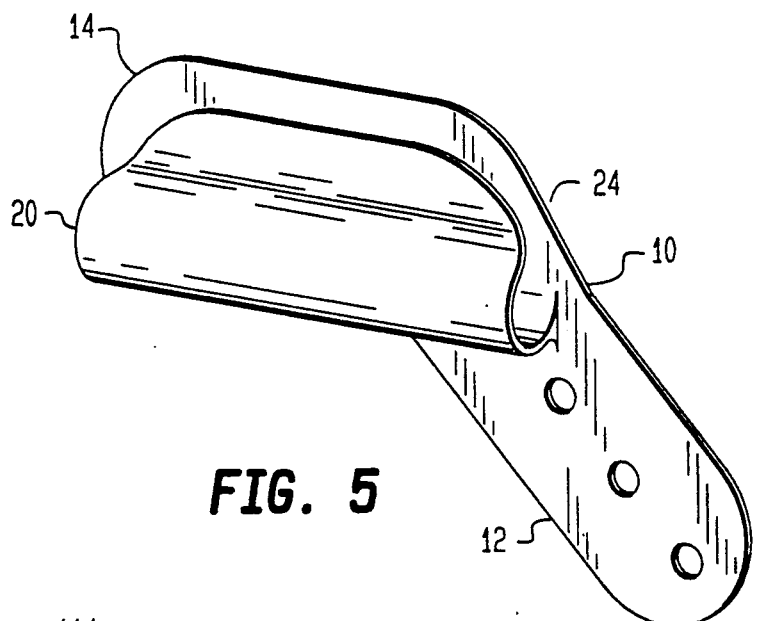
FIG. 5 is a perspective view of the turbinate sheath of FIGS. 1-4.

Referring to FIGS. 1-5 of the drawing, the new turbinate sheath device is depicted. A pair of resilient septal plate members 10 and 10L are shown spaced apart as they would be on opposite sides of the septum (not shown). Each of the plate members 10, 10L having a front plate portion 12 and rear plate portion 14 joined at an obtuse angular transition portion 15, with each of the septal plate members having an arcuate upper edge portion 16 corresponding to the obtuse angular transition portion. Each of the septal plate members has an integrally formed turbinate sheathing portion 20, 20L extending along an outer surface of the rear plate portion 14 in a substantially horizontal position, with the turbinate sheathing portion being formed into a U-shape with an upper open slot portion 22 adapted to receive and hold the middle turbinate during post-operative healing. Means for securing the pair of septal plate members 10, 10L in opposing positions can be provided by perforating the front plate portion 12 with a plurality of spaced apart apertures 26 to permit transfixation suturing.

Advantageously, the turbinate sheathing portion 20 extends outwardly from the rear plate portion 14 at a mid-portion thereof with a reverse curved sheathing wall 23 laterally spaced from the rear plate portion 14 to form the open slot. As shown, the sheathing wall has an elongated horizontal portion 24 adapted to grip the middle turbinate and an outward flare portion 22 adapted to guide the turbinate sheathing portion over the middle turbinate during insertion. In the preferred embodiments, the device may be formed of medically acceptable, thermoplastic, flexible perfluoroethylene polymer (e.g.- teflon or the like), and is designed so that the septal plate member 10 and turbinate sheathing portion 20 are substantially uniformly thick and are formed with rounded corners. It is understood that the materials of construction are chosen according to safe medical practice and fabrication methods. Suitable materials for injection molding of the device include poly(-vinyl chloride) or polyethylene; however, haloethylene polymers, silicones, polyesters, etc. may be employed by thermal forming, milling, etc.

Although the dimensions may be varied according to patient size and operating technique, in typical adult human use the turbinate sheathing portion 20 extends longitudinally parallel to the rear plate portion about 30-50 mm and has a height of about 13-15 mm.

The device according to FIGS. 1-5 is particularly useful in surgical procedures where the nasal septum requires a splint during healing. The full plate surface extending from the front plate portion 12 to the rear portion 14 provides the septum with adequate dimensional stability and support. The front plate portion, however, may be shortened as depicted in FIGS. 6 and 7.

Figure 6:
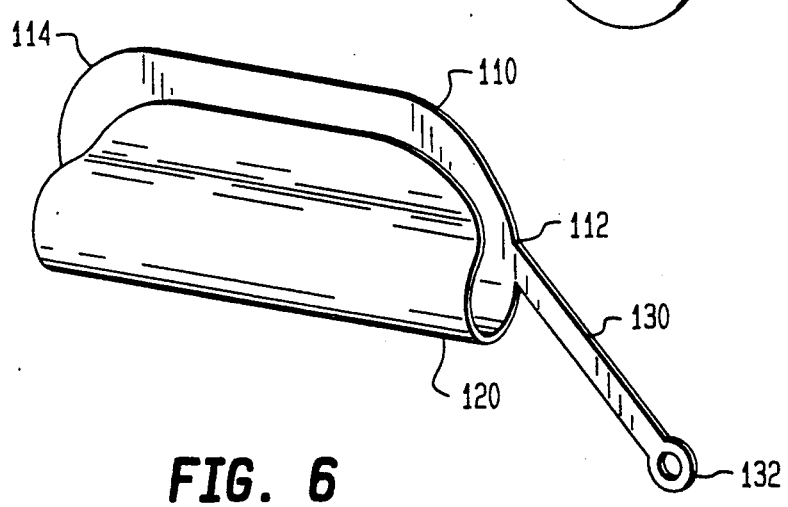
FIGS. 6 and 7 are perspective views of alternative embodiments of the invention.

In FIG. 6, the sheath plate 110 is truncated at the distal end adjacent the turbinate sheathing portion 120. A thin, integrally molded, plate extension 130 is angularly disposed outwardly and downwardly from plate portion 110, terminating in a suture hole 132 to provide attachment means for an opposite sheath element (not shown). The plate extension element 130 retains the main turbinate sheathing portion and rear plate portion 114 in the desired position during healing to prevent distal slippage. The extension tab 130 may be secured to the septum by suturing.

Figure 7:
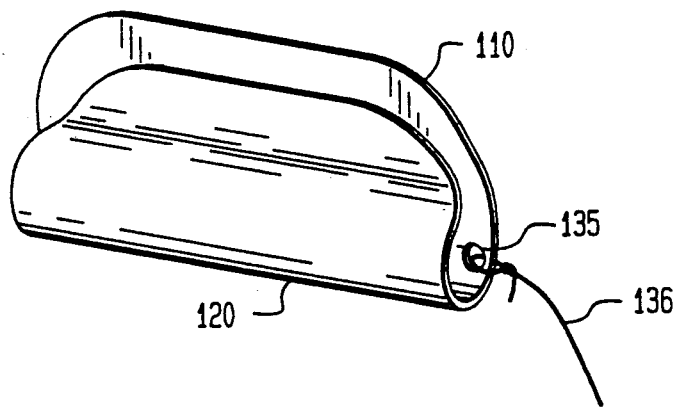

If the gripping action of the turbinate sheath portion 120, is adequate to prevent shifting of the glove-like device, the configuration of FIG. 7 may be employed, wherein the front plate portion 12 (compare FIG. 5), is eliminated. Hole 135 is located on the distal end of plate portion 110 to permit attachment via suture or cord 136, thus preventing loss of the turbinate sheath in the event of loosening during use.

Often medical devices of disposable plastic materials are sterilized and packaged as a surgical kit, and it is contemplated that such a kit be assembled from a sealable envelope containing a nasal tampon material and the turbinate sheath device as described herein.

The present invention is shown to be efficacious in endoscopic nasal surgery wherein the human middle turbinate, contiguous paranasal sinuses and/or nasal septum are subjected to surgical procedure by applying to the post-operative middle turbinate through opposite nasal passages a pair of turbinate sheath element members, substantially as described and shown in FIGS. 1-7, and securing the pair in position overlying the middle turbinate, thereby separating the middle turbinate from the nasal septum to prevent medial adhesion and separating the middle turbinate from the nasal wall to prevent lateral adhesion during healing. The procedure is particularly useful in human ethmoidectomy surgery by inserting and guiding the turbinate sheathing portion over the middle turbinate during insertion, gripping the middle turbinate, and securing the septal plate member in position.

The device is also useful where simultaneous septoplasty is performed on the nasal septum and the pair of septal plate members is secured on opposite sides of the nasal septum for support thereof to promote straight healing.

While the turbinate sheath device has been described by particular examples, there is no intent to limit the inventive concept except as set forth in the claims.

I claim:

1. A turbinate sheath device for post-operative separation of the human middle turbinate from the adjacent nasal septum, comprising:

a pair of resilient septal plate members adapted for insertion on opposite sides of the septum, each of said plate members having a front plate portion and rear plate portion joined at an obtuse angular transition portion; each of said septal plate members having an arcuate upper edge portion corresponding to the obtuse angular transition portion;

each of said septal plate members having an integrally formed turbinate sheathing portion extending along an outer surface of said rear plate portion in a substantially horizontal position, said turbinate sheathing portion being U-shaped with an upper open slot portion adapted to receive and hold the middle turbinate during post-operative healing; and means for securing the pair of septal plate members in opposing positions, whereby the middle turbinate is separated from the septum and lateral nasal wall to prevent adhesion.

2. The device of claim 1 wherein the turbinate sheathing portion extends outwardly from the rear plate portion at a mid-portion thereof with a reverse curved sheathing wall laterally spaced from the rear plate portion to form said slot portion, wherein the sheathing wall has an elongated horizontal portion adapted to grip the middle turbinate and an outward flare portion adapted to guide the turbinate sheathing portion over the middle turbinate during insertion.

3. The device of claim 1 wherein the front plate portion has a plurality of spaced apart apertures to permit transfixation suturing.

4. The device of claim 1 which is formed of medically acceptable, thermoplastic, flexible perfluoroethylene polymer.

5. The device of claim 1 wherein the septal plate member and turbinate sheathing portion are substantially uniformly thick and are formed with rounded corners.

6. The device of claim 1 wherein the turbinate sheathing portion extends longitudinally parallel to the rear plate portion about 30-50 mm and has a height of about 13-15 mm.

7. A turbinate sheath device for post-operative separation of the human middle turbinate from the nasal septum and lateral nasal wall, comprising:
 a pair of resilient septal plate members adapted for insertion on opposite sides of the septum, each of said septal plate members having a front plate portion and rear plate portion and an integrally formed turbinate sheathing portion extending along an outer surface of said plate member in a substantially horizontal position, said turbinate sheathing portion being U-shaped with an upper open slot portion adapted to receive and hold the middle turbinate during post-operative healing,
 said turbinate sheathing portion extending outwardly from the plate member at a mid-portion thereof with a reverse curved sheathing wall laterally spaced from the rear plate portion to form said slot portion, wherein the sheathing wall has an elongated horizontal portion adapted to grip the middle turbinate and an outward flare portion adapted to guide the turbinate sheathing portion over the middle turbinate during insertion; and
 means for securing the pair of septal plate members in position overlying the middle turbinate, whereby the middle turbinate is separated from the septum to prevent medial adhesion and separated from the nasal wall to prevent lateral adhesion.

8. A surgical kit comprising a sealable envelope, nasal tampon material and the turbinate sheath device according to claim 7.

9. In an endoscopic nasal surgery method wherein the human middle turbinate, contiguous paranasal sinuses or nasal septum is subjected to surgical procedure, an improved post-operative healing technique which comprises:
 applying to the post-operative middle turbinate through opposite nasal passages a pair of resilient septal plate members adapted for insertion on opposite sides of the nasal septum, each of said septal plate members having a front plate portion and rear plate portion and an integrally formed turbinate sheathing portion extending along an outer surface of said plate member in a substantially horizontal position, said turbinate sheathing portion being U-shaped with an upper open slot portion adapted to receive and hold the middle turbinate during post-operative healing; said turbinate sheathing portion extending outwardly from the plate member at a mid-portion thereof with a reverse curved sheathing wall laterally spaced from the rear plate portion to form said slot portion, wherein the sheathing wall has an elongated horizontal portion adapted to grip the middle turbinate and an outward flare portion adapted to guide the turbinate sheathing portion over the middle turbinate during insertion; and
 securing the pair of septal plate members in position overlying the middle turbinate, thereby separating the middle turbinate from the nasal septum to prevent medial adhesion and separating the middle turbinate from the nasal wall to prevent lateral adhesion during healing.

10. The endoscopic nasal surgery method of claim 9 wherein simultaneous septoplasty is performed on the nasal septum and the pair of septal plate members is secured on opposite sides of the nasal septum for support thereof to promote straight healing.

11. In human ethmoidectomy, frontal sinusotomy, maxillary antrostomy, or sphenoidectomy surgery wherein the human middle turbinate is subjected to surgical procedure, an improved post-operative healing technique which comprises:
 inserting over at least a portion of the post-operative middle turbinate a turbinate sheath device comprising a septal plate member having a front plate portion and rear plate portion and an integrally formed turbinate sheathing portion extending along an outer surface of said rear plate portion in a substantially horizontal position, said turbinate sheathing portion extending outwardly from the plate member with a curved sheathing wall laterally spaced from the rear plate portion to form a slot portion, wherein the sheathing wall has an elongated horizontal portion,
 guiding the turbinate sheathing portion over the middle turbinate during insertion and gripping the middle turbinate, and
 securing the septal plate member in position overlying the middle turbinate, whereby the middle turbinate is separated from the septum to prevent medial adhesion and separated from the nasal wall to prevent lateral adhesion.

* * * * *